(12) United States Patent
Horn

(10) Patent No.: US 8,952,011 B2
(45) Date of Patent: Feb. 10, 2015

(54) COMPOSITIONS AND METHODS FOR THE TREATMENT OF NASAL CONDITIONS

(71) Applicant: Eye Therapies, LLC, Dana Point, CA (US)

(72) Inventor: Gerald Horn, Deerfield, IL (US)

(73) Assignee: Eye Therapies LLC, Dana Point, CA (US)

( * ) Notice: Subject to any disclaimer, the term of this patent is extended or adjusted under 35 U.S.C. 154(b) by 0 days.

(21) Appl. No.: 14/010,340

(22) Filed: Aug. 26, 2013

(65) Prior Publication Data

US 2013/0345229 A1   Dec. 26, 2013

Related U.S. Application Data

(63) Continuation-in-part of application No. 13/066,370, filed on Apr. 13, 2011, which is a continuation-in-part of application No. 12/460,967, filed on Jul. 27, 2009.

(60) Provisional application No. 61/137,714, filed on Aug. 1, 2008, provisional application No. 61/192,777, filed on Sep. 22, 2008, provisional application No. 61/203,120, filed on Dec. 18, 2008, provisional application No. 61/207,481, filed on Feb. 12, 2009.

(51) Int. Cl.

| A01N 43/58 | (2006.01) |
|---|---|
| A01N 43/60 | (2006.01) |
| A61K 31/50 | (2006.01) |
| A61K 31/495 | (2006.01) |
| A61K 31/498 | (2006.01) |
| A61K 9/00 | (2006.01) |
| A61K 9/08 | (2006.01) |
| A61K 47/10 | (2006.01) |
| A61K 47/32 | (2006.01) |
| A61K 47/38 | (2006.01) |

(52) U.S. Cl.
CPC ............. *A61K 31/498* (2013.01); *A61K 9/0043* (2013.01); *A61K 9/0048* (2013.01); *A61K 9/08* (2013.01); *A61K 47/10* (2013.01); *A61K 47/32* (2013.01); *A61K 47/38* (2013.01)
USPC ........................................................ 514/249

(58) Field of Classification Search
USPC ........................................................ 514/249
See application file for complete search history.

(56) References Cited

U.S. PATENT DOCUMENTS

| 4,663,340 A | 5/1987 | Najer et al. |
|---|---|---|
| 5,021,416 A | 6/1991 | Gluchowski |
| 5,300,504 A | 4/1994 | Gluchowski |
| 5,304,569 A | 4/1994 | Lammintausta et al. |
| 5,424,078 A | 6/1995 | Dziabo et al. |
| 5,561,132 A | 10/1996 | Burke et al. |
| 5,605,911 A | 2/1997 | Olney et al. |
| 5,677,321 A | 10/1997 | Jeon et al. |
| 5,712,301 A | 1/1998 | Heinonen et al. |
| 5,756,503 A | 5/1998 | Burke et al. |
| 5,804,587 A | 9/1998 | Cupps et al. |
| 5,948,414 A | 9/1999 | Wiersma |
| 5,948,804 A | 9/1999 | Jeon et al. |
| 5,965,595 A | 10/1999 | Maurer et al. |
| 6,040,451 A | 3/2000 | Jeon et al. |
| 6,087,361 A | 7/2000 | Munk et al. |
| 6,110,952 A | 8/2000 | Henry et al. |
| 6,117,871 A | 9/2000 | Maurer et al. |
| 6,159,998 A | 12/2000 | Jeon et al. |
| 6,162,818 A | 12/2000 | Henry et al. |
| 6,194,415 B1 | 2/2001 | Wheeler et al. |
| 6,242,442 B1 | 6/2001 | Dean et al. |
| 6,248,741 B1 | 6/2001 | Wheeler et al. |
| 6,465,464 B2 | 10/2002 | Wheeler et al. |
| 6,534,048 B1 | 3/2003 | Borgman |
| 6,562,855 B1 | 5/2003 | Franks et al. |
| 6,562,873 B2 | 5/2003 | Olejnik et al. |
| 6,627,210 B2 | 9/2003 | Olejnik et al. |
| 6,641,834 B2 | 11/2003 | Olejnik et al. |
| 6,653,354 B2 | 11/2003 | Franks et al. |
| 6,673,337 B2 | 1/2004 | Olejnik et al. |
| 6,730,065 B1 | 5/2004 | Horn |
| 6,916,811 B2 | 7/2005 | Boyle et al. |
| 6,982,079 B2 | 1/2006 | Huth |
| 7,030,149 B2 | 4/2006 | Chang et al. |
| 7,232,837 B2 | 6/2007 | Booth et al. |
| 7,309,706 B2 | 12/2007 | Rupp et al. |
| 7,589,057 B2 | 9/2009 | Chang et al. |
| 7,678,829 B2 | 3/2010 | Matier et al. |
| 2001/0948001 | 9/2001 | Chow et al. |

(Continued)

FOREIGN PATENT DOCUMENTS

| WO | 2009022096 A1 | 2/2009 |
|---|---|---|
| WO | 2009124755 A1 | 4/2009 |

OTHER PUBLICATIONS

Mechanism of decongestant activity of x2-adrenoceptor agnosits, Corboz M.R. et al., Pulmonary Pharmacology & Therapeutics 21 (2008) 449-454.

Alpha-adrenoceptor agonistic activity of oxymetazoline and xylometazoline, Haenisch B. et al., Fundam Clin Pharmacol. Dec. 17, 2009.

An Evaluation of Nasal Response Following Different Treatment Regimes of . . . , Morris S. et al., American Journal Rhinology, vol. 11, No. 2, Mar.-Apr. 1997, pp. 109-115.

(Continued)

*Primary Examiner* — Marcos Sznaidman
(74) *Attorney, Agent, or Firm* — Wood, Phillips, Katz, Clark & Mortimer

(57) ABSTRACT

The invention provides compositions and methods for treating nasal congestion. The provided compositions and methods utilize low concentrations of selective α-2 adrenergic receptor agonists. The compositions preferably include brimonidine.

8 Claims, 2 Drawing Sheets
(2 of 2 Drawing Sheet(s) Filed in Color)

(56) References Cited

U.S. PATENT DOCUMENTS

| | | | |
|---|---|---|---|
| 2002/0037297 A1 | 3/2002 | Crespo et al. |
| 2002/0156076 A1 | 10/2002 | Chow et al. |
| 2002/0197300 A1 | 12/2002 | Schultz et al. |
| 2003/0181354 A1 | 9/2003 | Abdulrazik |
| 2003/0229088 A1 | 12/2003 | Donello et al. |
| 2004/0132824 A1 | 7/2004 | Donello et al. |
| 2004/0266776 A1 | 12/2004 | Gil et al. |
| 2005/0020600 A1 | 1/2005 | Scherer |
| 2005/0058696 A1 | 3/2005 | Donello et al. |
| 2005/0059664 A1 | 3/2005 | Gil et al. |
| 2005/0244468 A1 | 11/2005 | Huang et al. |
| 2005/0244474 A1 | 11/2005 | Huang et al. |
| 2006/0264442 A1 | 11/2006 | Ruiz et al. |
| 2006/0276495 A1 | 12/2006 | Salmun et al. |
| 2007/0031472 A1 | 2/2007 | Huang et al. |
| 2007/0203085 A1 | 8/2007 | Lang |
| 2008/0020076 A1 | 1/2008 | Jhamandas et al. |
| 2008/0131483 A1 | 6/2008 | Abdulrazik |
| 2008/0131485 A1 | 6/2008 | Huang et al. |
| 2008/0207627 A1 | 8/2008 | Gil et al. |
| 2008/0207628 A1 | 8/2008 | Gil et al. |
| 2009/0176843 A1 | 7/2009 | Bhat et al. |
| 2009/0220611 A1 | 9/2009 | Castan et al. |
| 2010/0028266 A1 | 2/2010 | Horn |
| 2010/0029659 A1 | 2/2010 | Horn |
| 2010/0029661 A1 | 2/2010 | Horn |
| 2010/0029662 A1 | 2/2010 | Horn |
| 2010/0029663 A1 | 2/2010 | Horn |

OTHER PUBLICATIONS

Pharmacological Characterization of Postjunctional a-Adrenoceptors in . . . , Corboz M.R. et al., American Jour of Rhinology, vol. 19, No. 5, Sep.-Oct. 2005, pp. 495-502.
Postjuntional a2-adrenoceptors in blood ve3ssels of human nasal mucosa, Ichimura K. et al., Arch Otorhinolaryngol (1988) 245:127-131.
Long-term use of oxy- and xylometazoline nasal sprays induces rebound swelling, tolerance, and nasal hyperreactivity, Graf P., Rhinology 1996, 34(1):9-13.
Alpha 1-receptors at pre-capillary resistance vessels of the human nasal mucosa, Johannssen V et al., Rhinology 1997; 35(4):161-65.
Correspondence A Propos De L'article: <<Traitement Des Glaucomes Par La Brimonidine>>, M. Detry-Morel ET C. Dutrieux< J Fr Ophtalmol.2001; 24(7): 748-9.
Potent a2A-Adrenoceptor-Mediated Vacoconstriction by Brimonidine in Porcine Ciliary Arteries, Anna Wikberg-matsson, et al., IOVS, 2001, vol. 42, No. 9, 2049-55.
Medical Management of Chronic Rhinosinusitus—Jean P. Font, MD, Matthew Ryan, MD (May 2006).
Interactions Between CA2+ and H+ and Functional Consequences in Vascular Smooth Muscle—C. Austin and S. Wray, Journ. of Amer. Heart Association (Circ. Res. 2000; 86:355-363).
Brimonidine: A Useful New Topical Treatment for Glaucoma and Ocular Hypertension—Drug Ther Perspect, Jan. 18, 1999, 13(1), 1-4.
Vartiainen, J, Dexmedetomidine-Induced Ocular Hyptension in rabbits with normal or elevated intraocular pressures, Invest. Ophthalmol. Vis. Sci. May 1992, 33(6), 2019-2023.
Silent Bedpartners—Nancy A. Collop, Chest 2002; 122, 1111-1112.
Traitment Des Glaucomes Par La Briminodine (Alphagan 0.2%)—M. Detry-Morel, C. Dutrieux, J. Fr. Opthamol., 2000; 23, 8, 763-768.
Vasopressin-Induced Vasoconstriction; Two Concentration-Dependen Signaling Pathways—Kyle K. Henderson and Kenneth L. Bryon, J. Appl. Physiol. 102: 1402-1409, 2007.
The Effect of Correction of Sleep-Disordered Breathing on Bp in Untreated Hypertension—K. Mae Hla, J.B. Skatrud, L. Finn, M. Palta and T. Young, Chest 2002:122 1125-1135.
Myogenic Tone and Reactivity of the Rat Opthalmic Artery—Y.P.R. Jarajapu, M.B. Grant, and H.J. Knot Invest. Opth. & Visual Science, Jan. 2004, vol. 45, No. 1.
Munoz, G, et al., Increased risk for flap dislocation with perioperative brimonidine use in femtosecond laser in situ keratomileusis, J Cataract Refact Surg 2009, 35, 1338-1342.
Prospective Study of the Association Between Sleep-Disordered Breathing and Hypertension—P. Peppard, et. al., The New England J. of Med, vol. 342, No. 19:1378:1384 (2000).
Rhinitis Medicamentosa—JT Ramey, E Bailen, RF LOckey, J. Investig. Allergol. Clin. Immunol. 2006; vol. 16(3); 148-155.
Characterization of three inhibitors of endothelial nitric oxide synthase in vitro and in vivo—D.D> Rees, et al., br. J. Pharmacol. (1990) 101, 746-752.
Inhibition of a-adrenergic vasoconstriction in exercising human thigh muscles—D. Walter Wray, et al., J. Physiol. 555, 2 pp. 545-564 (2003).
Dexmedetomidine Enhances the Local Anesthetic Action of Lidocaine via . . . Tatsushi Yoshitomi DDS et al., Anesth. Analg. 2008I 107:96-101.
Adding Dexmedetomidine to Lidocaines for Intravenous Regional Anesthesia, Dilek Memis, MS et. al, Anesth. Analg. 2004:98:835-40.
Hardman et al., Goodman and Gilman's the pharmacological basis of therapeutics: 10th edition, Aug. 28, 2001, p. 3-29, McGraw-Hill Professional.
Cantor, Louis B., Brimonidine in the treatment of glaucoma and ocular hypertension, Ther. Clin. Risk Manag., Dec. 2006, 2(4), 337-346.
Gilsbach et al., Genetic dissection of a2-adrenoceptor functions in adrenergic versus nonadrenergic cells, Molecular Phar 2009, 75(5), p. 1160-1170.
Sato et al., In Silico Functional Profiling of Small Molecules and Its Applications, Journal of Medical Chemistry 2008, 51(24), 7705-7716 (Abstract).
Lehtimaeki et al., In vitro and in vivo profiling of fadolmidine, a novel potent a2-adrenoceptor agonist with local mode of action, European Journal of Pharmacology 2008, 599(1-3), 65-71 (Abstract).
Verbruggen et al., The effect of intravenous medetomidine on pupil size and intraocular pressure in normotensive dogs, Veterinary Quarterly 2000, 22(3), 179-180 (Abstract).
Wong et al., Design and synthesis of alpha2 adrenoceptor agonists, Book of Abstracts, 213th ACS National Meeting, San Francisco, Apr. 13-17 (1997), MEDI-023, American Chemical Society: Washington, D.C., (Abstract).
Ogidigben et al., Comparative effects of alpha-2 and DA-2 agonists on intraocular pressure in pigmented and nonpigmented rabbits, Journal of Ocular Pharmacology 1993, 9(3), 187-99 (Abstract).
MacDonald et al., Comparison of the cardiovascular effects of the a2-adrenoceptor agonist, dexmedetomidine, in rats and rabbits, Drug Development Research 1993, 28(4), 473-477 (Abstract).
Jin et al., Ocular hypotensive effects of medetomidine and its analogs, Journal of Ocular Pharmacology 1991, 7(4) 285-296 (Abstract).
Laengle et al., GLC756 decreases TNF-alpha via an alpha2 and beta2 adrenoceptor related mechanism, Experimental eye research, Nov. 2006, 83(5), 1246-1251 (Abstract).
Stamer et al., Cultured human trabecular meshwork cells express functional alpha 2A adrenergic receptors, Investigative ophthalmology & visual science Nov. 1996, 37(12), 2426-2433 (Abstract).
Pate et al., Ophthalmic arachidonylethanolamide decreases intraocular pressure in normotensive rabbits, Current eyer research Sep. 1995, 14(9), 791-797 (Abstract).
Jin et al., Ocular a2-receptor subclasses and antiglaucoma efficacy, Journal of Ocular Pharmacology, 1994, 10(1), 359-369 (Abstract).
Potter et al., Review: Alpha2 and DA2 agonists as antiglaucoma agents: Comparative pharmacology and clinical potential, Journal of Ocular Pharmacology, 1990, 6(3), 251-257 (Abstract).
Kost et al., Procedural Sedation and Analgesia in the Pediatric Emergency Department: A Review of Sedative Pharmacology, Clinical Pediatric Emergency Medicine, Dec. 2010, 11(4), 233-243 (Abstract).
Penha et al., Retinal and ocular toxicity in ocular application of drugs and chemicals—Part I: Animal models and toxicity assays, Ophthalmic Research, Jul. 2010, 44(2), 82-104 (Abstract).
Mowafi et al., Effect of dexmedetomidine premedication on the intraocular pressure changes after succinylcholine and intubation, British Journal of Anaesthesia, Apr. 2008, 100(4), 485-489.

(56) References Cited

OTHER PUBLICATIONS

Mowafi et al., Remifentanil obtunds intraocular pressure rises associated with suxamethonium, British Journal of Anaesthesia, Sep. 2008, 101(3), 432-433.
Bielory, Chirality in ocular agents, Current Opinion in Allergy and Clinical Immunology, Oct. 2007, 7(5), 418-423 (Abstract).
Freeman, Hypoxic-ischaemic brain injury (HIBI) after cardiopulmonary arrest, Current Anaesthesia and Critical Care, 2007, 18(5-6), 261-276 (Abstract).
Crassous et al., Interest of a2-adrenergic agonists and antagonists in clinical practice: Background, facts and perspectives, Current Topics in Medicinal Chemistry, Jan. 2007, 7(2), 187-194 (Abstract).
Gentili et al., Agonists and antagonists targeting the different a2-adrenoceptor subtypes, Current Topics in Medicinal Chemistry, Jan. 2007, 7(2), 163-186 (Abstract).
Weber et al., Neuroprotective effects of a2-adrenergic receptor agonists, Drug News and Perspectives, Apr. 2007, 20 (3), 149-154 (Abstract).
Loots, Agents for sedation in ophthalmic surgery: A review of the pharmacodynamics and clinical applications, Current Anaesthesia and Critical Care, 2006, 17(3-4), 179-190 (Abstract).
Robertson, Standing sedation and pain management for ophthalmic patients, Veterinary Clinics of North America—Equine Practice, Aug. 2004, 20(2), 485-497 (Abstract).
Ruffolo et al., a-Adrenoceptors, Pharmacology and Therapeutics, 1994, 61(1-2), 1-64 (Abstract).
Tripathi et al., Role of receptors in the trabecular meshwork of the eye as targeted to the development of antiglacoma therapy, Drug Development Research, 1992, 27(3), 1991-228 (Abstract).
Georgiou et al., Changes in NMDA receptor contribution to synaptic transmission in the brain in a rat model of glaucoma, Neurobiology of Disease, Sep. 2010, 39(3), 344-351 (Abstract).
Schoewald et al., Relationship between Steroid Permeability across Excised Rabbit Cornea and Octanol-Water Partition Coefficients, Journal of Pharmaceutical Scienses, Jun. 1978, 67(6), 786-788.
Chang et al., Improved Corneal Penetration of Timolol by Prodrugs as a Means to Reduce Systemic Drug Load, 1987, 28(3), 487-491.
Li et al., A Study of the Relationship between Cornea Permeability and Eye Irritation Using Membrane-Interaction QSAR Analysis, Toxicological Sciences, 2005, 88(2), 434-446.
Forster, et al., Adrenergic Alpha1, and Alpha2 Binding Sites are Present in Bovine Retinal Blood Vessels, Investigative Ophthalmology & Visual Science, 1987, 28(11), 1741-1746.
Donello et al., a2-Adrenoceptor Agonists Inhibit Vitreal Glutamate and Aspartate Accumulation and Preserve Retinal Function after Transient Ischemia, Journal of Pharmacology and Experimental Therapeutics, 2011, 296(1), 216-223.
Akasu et al., Reduction of the N-Type Calcuium Current by Noradrenaline in Neurones of Rabbit Vesical Parasympathetic Ganglia, Journal of Physiology, 1990, 426, 439-452.
Trendelenburg et al., a2-Adrenoceptor-mediated inhibition of cultured sympathetic neurons: changes in a2A/D-adrenoceptor-deficient mice, Naunyn-Schmiedeberg's Arch Pharmacology, 2011, 363, 110-119.
Dong et al., a2 Adrenergic Modulation of NMDA Receptor Function as a Major Mechanism of RGC Protection in Experimental Glaucoma and Retinal Excitotoxicity, Investigative Ophthalmology & Visual Science, Oct. 2008, 49(10), 4515-4522.
Saylor et al., Experimental and Clinical Evidence for Brimonidine as an Optic Nerve and REtinal Neuroprotective Agent, Arch Ophthalmol, Apr. 2009, 127(4), 402-406.
Shirasaka et al., Activation of a G Protein-coupled Inwardly Rectifying K+ Current and Suppression of Ih Contribute to Dexmedetomidine-induced Inhibition of Rat Hypothalamic Paraventricular Nucleus Neurons, Anesthesiology, 2007, 107, 605-615.
Rosa et al., Brimonidine evokes hetrogenous vasomotor response of retinal arterioles: diminished nitric oxide-mediated vasodilation when size goes small, Am J Physiol Heart Cir Physiol 2006, 291, H231-H238.
Wirostoko et al., The Vascular Theory in Glaucoma, Glaucoma Today, Apr. 2009, 25-27.
Huang et al., The two sides of cytokine signaling and glaucomatous optic neuropathy, j ocul biol dis inform, 2009, 2, 98-103.
Hamasaki et al., Dual a2-Adrenergic Agonist and a1-Adrenergic Antagonist Actions of Dexmedetomidine on Human Isolated Endothelium-Denuded Gastroepiploic Arteries, Anesth Analg, 2002, 94, 1434-1440.
Paris et al., The Anesthetic Effects of Etomidate: Species-Specific Interaction with a2-Adrenoceptors, Anesth Analg. 2007, 105(6), 1644-1649.
Pertovaara, Antinociceptive Properties of Fadolmidine (MPV-24-26), a Novel a2-Adrenoceptor Agonist, CNS Drug Reviews, 2004, 10(2), 117-126.
Niemi et al., Synthesis, hydrolysis, and intraocular pressure lowering effects of fadolmidine prodrugs, International Journal of Pharmaceutics 2005, 29, 121-127.
Vaidyanathan S. et al., Fluticasone Reverses Oxymetazoline-induced Tachyphylaxis of Response and Rebound Congestion, American Journal of Respiratory and Critical Care Medicine vol. 182, 19-24, 2010.

COMPOSITIONS AND METHODS FOR THE TREATMENT OF NASAL CONDITIONS

CROSS-REFERENCE TO RELATED APPLICATIONS

This application is a continuation-in-part of U.S. patent application Ser. No. 13/066,370 filed Apr. 13, 2011, which is a continuation-in-part of U.S. patent application Ser. No. 12/460,967 filed Jul. 27, 2009, which claims a priority to U.S. Provisional Application Ser. Nos. 61/137,714, filed on Aug. 1, 2008; 61/192,777, filed on Sep. 22, 2008; 61/203,120, filed on Dec. 18, 2008; and 61/207,481 filed on Feb. 12, 2009. The contents of the above-mentioned applications are hereby incorporated by reference in their entirety.

BACKGROUND OF THE INVENTION

Adrenergic receptors mediate physiological responses to the catecholamines, norepinephrine and epinephrine, and are members of the superfamily of G protein-coupled receptors having seven transmembrane domains. These receptors, which are divided pharmacologically into $\alpha$-1, $\alpha$-2 and $\beta$-adrenergic receptor types, are involved in diverse physiological functions including functions of the cardiovascular and central nervous systems. The $\alpha$-adrenergic receptors mediate excitatory and inhibitory functions: $\alpha$-1 adrenergic receptors are typically excitatory post-synaptic receptors which generally mediate responses in an effector organ, while $\alpha$-2 adrenergic receptors are located postsynaptically as well as presynaptically, where they inhibit release of neurotransmitters. The $\alpha$-adrenergic receptors also mediate vascular constriction. Agonists of $\alpha$-2 adrenergic receptors currently are used clinically in the treatment of hypertension, glaucoma, spasticity, and attention-deficit disorder, in the suppression of opiate withdrawal, as adjuncts to general anesthesia and in the treatment of cancer pain.

$\alpha$-2 adrenergic receptors are present in various bodily organs, including eyes and nose. It is believed that they play a role in nasal congestion, among many other diseases.

$\alpha$-2 adrenergic receptors are presently classified into three subtypes based on their pharmacological and molecular characterization: $\alpha$-2 A/D ($\alpha$-2A in human and $\alpha$-2D in rat); $\alpha$a-2B; and $\alpha$-2C (Bylund et al., Pharmacol. Rev. 46:121-136 (1994); and Hein and Kobilka, Neuropharmacol. 34:357-366 (1995)). The $\alpha$-2A, $\alpha$-2B, and $\alpha$-2C subtypes appear to regulate arterial and/or venular contraction in some vascular beds, and the $\alpha$-2A and $\alpha$-2C subtypes mediate feedback inhibition of norepinephrine release from sympathetic nerve endings.

Many compounds having selective $\alpha$-2 agonist activity are known and include brimonidine (which has been used for lowering intraocular pressure in patients with open-angle glaucoma or ocular hypertension), guanfacine (which has been used to control high blood pressure), dexmedetomidine (which has been used as a sedative, analgesic, sympatholytic and anxiolytic), and methyl dopa (which has been used as a centrally-acting adrenergic antihypertensive).

Nasal conditions, such as nasal congestion, cause inconvenience and suffering to many individuals. The use of conventional decongestant nasal sprays cause rebound congestion, often lasting 24 hours or longer, which typically results after using these sprays for more than three consecutive days, or even after a single day's use. In addition, continued use of conventional nasal decongestants (such as Afrin®, Afrin is a registered trademark of MSD Consumer Care, Inc.; Dristan®, Dristan is a registered trademark of Wyeth LLC; and many others) may result in chronic and long term inflammatory pathological conditions. These conditions frequently occur as a subject attempts to reverse the rebound congestion with more and more frequent use of the conventional nasal decongestant. Phenylephrine, a strong $\alpha$-1 agonist, and oxymetazoline, a strong $\alpha$-1 agonist with some $\alpha$-2 agonist activity, are powerful nasal decongestants. However, these decongestants are associated with numerous side effects upon repeat use. Rhinitis medicamentosa is one such result side effect that results from inflammatory ischemic changes caused by such patterns of use. Rhinitis medicamentosa ultimately results in a total nasal blockage which may not be relieved by simply stopping the medication. It may take days, weeks, months, or even medical or surgical intervention to treat rhinitis medicamentosa. It is currently estimated that 10 million people in the U.S. alone suffer from this condition.

It is a long held dogma of prior art that all topical $\alpha$-agonists when used nasally induce vasoconstriction, and as a result, cause ischemia. Thus, it is thought that all topical $\alpha$-agonists, when repeatedly topically applied to mucosal surfaces, result in rebound hyperemia and/or congestion, tachyphylaxis, and chronic ischemic inflammatory change, such as rhinitis medicamentosa.

Thus, there is a need in the art for new compositions and methods that would be useful for treatment of nasal conditions, including but not limited to nasal congestion, which cause long lasting relief with no or only transient (i.e., only a few hours, with very low incidence) rebound congestion and no rhinitis medicamentosa. There is also a need for new formulations for medications useful for the treatment of nasal congestion, whereby said medications can be administered through the nasal route to relieve nasal congestion on a regular basis without significant rebound congestion and/or rhinitis medicamentosa.

SUMMARY OF THE INVENTION

The present invention provides compositions and methods for treating a nasal condition by administering low concentrations of highly selective $\alpha$-2 adrenergic receptor agonists to a subject in need thereof.

The provided compositions and methods utilize low concentrations of highly selective $\alpha$-2 adrenergic receptor agonists having a binding affinity of 100 fold or greater for $\alpha$-2 over $\alpha$-1 adrenergic receptors. The concentration of the selective $\alpha$-2 adrenergic receptor agonist is preferably below the concentration at which $\alpha$-1 adrenergic receptors are activated sufficiently enough to cause adverse ischemic vasoconstrictive consequences. Preferably, the concentration of the selective $\alpha$-2 adrenergic receptor agonist is below about 0.05% weight by volume of the composition.

In preferred embodiments of the invention, the selective $\alpha$-2 adrenergic receptor agonist is selected from the group consisting of lofexidine, apraclonidine, mivazerol, brimonidine, alpha methyl dopa, guanfacine, fadolmidine, dexmedetomidine, (+)-(S)-4-[1-(2,3-dimethyl-phenyl)-ethyl]-1,3-dihydro-imidazole-2-thione, 1-[(imidazolidin-2-yl)imino]indazole, and mixtures of these compounds.

In a preferred embodiment, a pH of the composition comprising the selective $\alpha$-2 adrenergic receptor agonist is between about 4.0 and about 8.5. If it is desired to achieve a more effective topical mucosal application with minimal mucosal penetration (for example, in such conditions as vasomotor rhinitis or nasal congestion), then it is generally preferred to maintain pH of the composition between about 4.0 and about 6.5. If, on the other hand, it is desired to achieve a deeper mucosal penetration (for example, delivery of drugs intravascularly), then a preferred pH of the composition may be between about 6.0 and about 8.0.

If more prolonged effect is desired nasally than two to three sprays per naris about one minute apart may be preferred, each spray optionally directed from tip to mid turbinate to superior turbinate. If delivery of central nervous system drug particularly a drug directed to the cerebral cortex is desired than delivery primarily to the superior turbinate via deeper penetration of the tip into the nares may be preferred.

In one embodiment of the invention, the compositions of the invention can be administered by nasal delivery. In another embodiment of the invention, the compositions of the invention can be administered by topical ophthalmic delivery.

In another embodiment of the invention, the composition further comprises pharmaceutically acceptable excipients selected from the group consisting of preservatives, vehicles, tonicity adjustors, pH adjustors and permeation enhancers.

In another embodiment, the invention is directed to a method of treating a nasal condition including but not limited to insufficient nares patency for peak athletic performance, rhinitis medicamentosa secondary to oxymetazoline nasal spray, allergic rhinitis, vasomotor rhinitis, sleep apnea, nasal secretion induced gastroesophogeal reflux, sleep apnea due to obstructed or partially obstructed turbinates, and treatment of partial or complete nasal obstruction due to nasal polyps or a combination thereof.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Definitions

Figure 1:
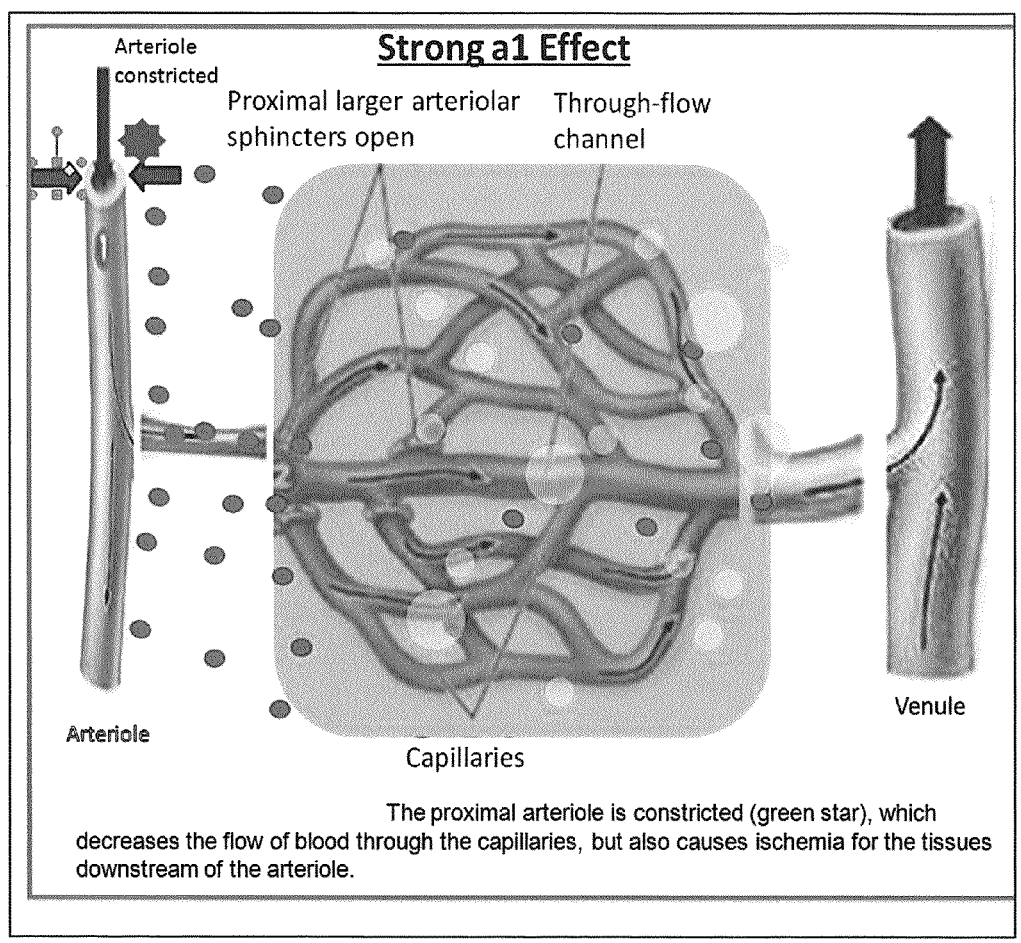
FIG. 1 is a graphical representation of the effects of activating α-1 adrenergic receptors.

For purposes of the present invention, the terms below are defined as follows.

The term "low concentrations" refers to concentrations from between about 0.0001% to about 0.065%; more preferably, from about 0.001% to about 0.035%; even more preferably, from about 0.01% to about 0.035%; and even more preferably, from about 0.030% to about 0.035% weight by volume of the composition.

The term "brimonidine" encompasses, without limitation, brimonidine salts and other derivatives, and specifically includes, but is not limited to, brimonidine tartrate, 5-bromo-6-(2-imidazolin-2-ylamino)quinoxaline D-tartrate, Alphagan® (Alphagan is a registered trademark of Allergan, Inc.), and UK14304.

The terms "treating" and "treatment" refer to reversing, alleviating, inhibiting, or slowing the progress of the disease, disorder, or condition to which such terms apply, or one or more symptoms of such disease, disorder, or condition.

The term "nasal condition" refers to any disease, disorder, or condition which affects and/or involves the nose. This term includes, but is not limited to, such conditions as nasal congestion, diseases and/or conditions associated with swollen nasal turbinates, all types of rhinitis including but not limited to vasomotor rhinitis and allergic rhinitis, sleep apnea, acute or chronic sinusitis, nasal polyposis, and any disease and/or condition associated with nasal discharge.

The term "substantial enlargement of nasal turbinates" refers to a significant enlargement of nasal turbinates, for example, more than about 50% compared to the baseline level of the subject so that it negatively affects the subject's breathing.

The term "subject" refers but is not limited to a person or other animal.

The term "over-the-counter" refers to components that can and have been used in pharmaceutical compositions that are sold in the United States without a prescription, because they have applied for and been approved for such use by the Food and Drug Administration or are exempt from the application process because they are generally recognized as safe and effective by medical professionals.

As used herein, all numerical values relating to amounts, weights, and the like, that are defined as "about" each particular value is plus or minus 10%. For example, the phrase "about 5% w/v" is to be understood as "4.5% to 5.5% w/v." Therefore, amounts within 10% of the claimed value are encompassed by the scope of the claims.

The term "% w/v" refers to the percent weight by volume of the total composition.

Embodiments of the Invention

It was surprisingly and unexpectedly found that selective alpha-2 (α-2) adrenergic receptor agonists (which are interchangeably referred to as "α-2 agonists" throughout the application) with extremely high selectivity for α-2 adrenergic receptors (meaning selectivity of at least 500:1 for α-2 over α-1 adrenergic receptors and preferably at least 900:1 cumulatively for α-2 subtypes A, B and C, and preferably predominantly for at least two of the three subtypes) at sufficiently low concentrations and at pH of between about 4.0 and about 8.5 can be used to treat a nasal condition in a subject in need thereof.

One example of a nasal condition is turbinate mucosal swelling which is caused by, or is contributed by, vasodilation and leakage of blood vessels. While not wishing to be bound to any particular theory, it is believed that vasodilation is after a short period of intense vasoconstriction of large and small arterioles associated with induced ischemia and inflammation inherent to such pervasive constriction consequent to α-1 adrenergic receptors activity. This α-1 effect is so dominant and fundamental to α-1 receptor activity it has been discovered via the present invention to occur not only after predominant α-1 agonist use, such as topical phenylephrine or tetrahydrozoline, but with α-2 agonists unless the binding affinity of α-2 agonists for α-2 over α-1 adrenergic receptors is sufficiently high, and the concentration sufficiently low to limit the pool of α-1 receptors inadvertently triggered. Otherwise, insufficiently highly selective α-2 agonists cause undesirable proportions of α-1 receptor stimulation with attendant ischemic vasoconstriction, proinflammatory cytokine release, and rebound vasodilation with repeat use such as is commonly found with agonists such as oxymetazoline.

Accordingly, the invention is directed to compositions and methods which employ highly selective α-2 agonists that have minimal α-1 agonist activity at extremely low concentrations, where for example 1% to 2% is considered extremely high, 0.5% to 1.0% still highly inductive of α-1 receptors and toxic for purposes of the present invention, 0.10% to 0.5% still too high, 0.070% to 0.10% still associated with a higher than preferred incidence of rebound, and only 0.065% or below potentially acceptable, where for most agonists, depending on degree of selectivity 0.050% or even more preferably 0.035% or less is desired. On the other hand some degree of useful activity may occur at one or more orders of magnitude further reduction of concentration. The compositions of the present invention preferentially stimulate α-2 adrenergic receptors so that α-1 adrenergic receptors are not stimulated sufficiently enough to cause vasodilation.

Thus, in one embodiment, the invention provides a method of treating a nasal condition comprising administering to a subject in need thereof a selective α-2 adrenergic receptor agonist having a binding affinity of 100 fold or greater for α-2 over α-1 adrenergic receptors, or a pharmaceutically acceptable salt thereof, wherein said selective α-2 adrenergic receptor agonist is present at a concentration below about 0.05% weight by volume.

In one embodiment, the invention provides compositions formulated for treating a condition associated with swollen nasal turbinates. Compositions particularly useful for these purposes preferably comprise brimonidine at concentrations of from about 0.01% to about 0.04%, and more preferably, from about 0.03% to about 0.035%. In a preferred embodiment, the condition associated with swollen nasal turbinates is selected from the group consisting of nasal congestion, allergic rhinitis, asthma, sleep disorders, and sleep apnea. A preferred pH of the composition formulated for the condition associated with swollen nasal turbinates is between about 6.5 and about 8.5.

Selective α-2 Adrenergic Receptor Agonists Suitable for the Purposes of the Invention Selective α-2 agonists that may be used for the purposes of the present invention have extremely high selectivity for α-2 adrenergic receptors, defined by their binding affinities ($K_i$) for α-2 over α-1 receptors of more than 100:1, more preferably 300:1; more preferably 500:1, even more preferably 700:1, even more preferably about 1000:1 or greater, and most preferably, 1500:1 or greater, where the ultimate preference may vary depending on the receptor mix of α-2 subtype activity for the particular species of mammal, and even further the ethnicity. In most cases subtypes A and B binding activity will be preferred over C for relief of local congestion; whereas subtype C binding activity may provide added value in some patients particularly for cerebral applications (e.g. migraine).

Not desiring to be bound by any specific theory or mechanism, it is believed that the particularly preferred adrenergic receptor agonists for most of the purposes of the present invention are highly selective for α-2B and/or α-2C receptors, as opposed to α-2A receptors.

In one embodiment, the selective α-2 adrenergic receptor agonist is a compound which has binding affinity of about 100 fold or greater for α-2 over α-1 adrenergic receptors, preferably about 300 fold or greater, more preferably about 700 fold or greater, even more preferably about 1000 fold or greater, and most preferably, about 1500 fold or greater.

The selective α-2 adrenergic receptor agonist may be present at a concentration from between about 0.0001% to about 0.05%; more preferably, from about 0.001% to about 0.035%; even more preferably, from about 0.01% to about 0.035%; and even more preferably, from about 0.03% to about 0.035% weight by volume.

It is preferred that a concentration of a selective α-2 adrenergic receptor agonist be below its vasoconstriction vs. concentration plateau. Typically, the optimal concentration is 10% to 90% above the minimal threshold of measurable vasoconstriction for a particular α-2 agonist, or below that of the plateau maximum concentration, and is preferably within the about 25% to about 75% range of either of these benchmarks. The term "plateau maximum concentration" means the concentration above which there is no or minimal further vasoconstriction effect. Other considerations in choosing a selective α-2 adrenergic receptor agonist are blood brain permeability and any possible side effects and other systemic reactions.

In one embodiment, the selective α-2 adrenergic receptor is selected from the group consisting of lofexidine, apraclonidine, mivazerol, brimonidine, alpha methyl dopa, guanfacine, fadolmidine, dexmedetomidine, (+)-(S)-4-[1-(2,3-dimethyl-phenyl)-ethyl]-1,3-dihydro-imidazole-2-thione, 1-[(imidazolidin-2-yl)imino]indazole, and mixtures of these compounds. Analogs of these compounds that function as highly selective α-2 agonists may also be used in compositions and methods of the present invention.

In a more preferred embodiment, the selective α-2 adrenergic receptor is brimonidine in the form of a salt. In a preferred embodiment, the salt is tartrate salt.

Compositions and Methods of the Invention

In one embodiment, the invention provides a composition comprising a selective α-2 adrenergic receptor agonist having a binding affinity of 100 or fold or greater for α-2 over α-1 adrenergic receptors, or a pharmaceutically acceptable salt thereof, for treating nasal congestion.

In a preferred embodiment, said selective α-2 adrenergic receptor agonist is present at a concentration below about 0.05% weight by volume, and more preferably, between about 0.001% to about 0.05% weight by volume.

In one embodiment, the selective α-2 adrenergic receptor agonist is selected from the group consisting of lofexidine, apraclonidine, mivazerol, clonidine, brimonidine, alpha methyl dopa, guanfacine, fadolmidine, dexmedetomidine, (+)-(S)-4-[1-(2,3-dimethyl-phenyl)-ethyl]-1,3-dihydro-imidazole-2-thione, 1-[(imidazolidin-2-yl)imino]indazole, and mixtures of these compounds.

In a preferred embodiment, the composition comprises brimonidine at a concentration between about 0.001% and about 0.035% weight by volume.

In a preferred embodiment, a pH of the composition comprising the selective α-2 adrenergic receptor agonist is between about 4.0 and about 8.5.

If it is desired to achieve a more effective topical mucosal application with minimal mucosal penetration (for example, in such conditions as vasomotor rhinitis or nasal congestion with substantial nasal discharge but relatively minimal turbinate swelling or physical blockage of nasal passages), then it is generally preferred to maintain pH of the composition between about 4.0 and about 6.5.

There is a direct relationship between a selective α-2 agonist's lipophilicity (as characterized by the Log D value) and the pH of a pharmaceutical composition containing the selective α-2 agonist: as the pH increases across the range of 4.0 to 8.5, the selective α-2 agonist's nonionic versus ionic equilibrium shifts to the left, so that its lipophilicity exponentially increases. This correlation is true for virtually all selective α-2 agonists, and in particular, brimonidine and dexmedetomidine, where such shift is relative to the intrinsic starting point—the Log P value—the lipophilicity at about pH 7.4 of the particular α-2 agonist.

Log D refers to a lipophilicity value at a given pH. This measurement is especially useful to determine the level of topical lipophilicity and resultant permeability of a topical composition. The higher the lipophilicity, the greater is the selective α-2 agonist's penetration through the lipophilic mucosal epithelial cell membranes. This is because at a more alkaline pH, more of the compound is present in a non-ionized form. When the pH is relatively low, e.g. between about 4.0 and about 6.5, the selective α-2 agonist is relatively less lipophilic and more ionized. As a result, a greater percentage of the selective α-2 agonist remains on the mucosa, increasing the drug's effectiveness as compared to the results at a higher pH. Thus, pH range of 4.0 to about 6.5, and more preferably 4.0 to 5.8, is preferred for the formulations for the treatment of nasal conditions involving serous nasal discharge without substantial turbinate swelling, such as vasomotor rhinitis.

If, on the other hand, it is desired to achieve a deeper mucosal penetration (for example, in such conditions as allergic rhinitis or sleep apnea; and generally in any nasal condition involving substantial enlargement of the nasal turbinates and/or physical blockage of nasal passages), then a preferred pH of the composition is between about 6.5 and about 8.5. At this higher pH, a greater proportion of the α-2 agonist will be non-ionized and more lipophilic, resulting in the greater permeation of the α-2 agonist through the lipophilic mucosal epithelial cell membranes. Thus, pH range of 6.5 to 8.5, and more preferably, 7.5 to 8.5 is preferred for formulations for intravascular drug delivery and or disorders associated with need for greater penetration of nasal turbinates, such as substantial enlargement of nasal turbinates and/or physical blockage of nasal passages, for example due to venous sinusoidal dilation as may occur in more severe cases of allergic rhinitis or turbinate blockage associated with sleep apnea with or without nodules causing some or complete blockage absent the present invention.

For some nasal conditions, it may be preferred to achieve a moderate lipophilicity, which is associated with pH of between about 5.6 and 6.2.

Dexmedetomidine has the following Log D values at different pH:
pH 4.0 to 5.6: Log D is 0.76 to 1.76;
pH 5.6 to 6.2: Log D is 1.76 to 2.28;
pH 6.2 to 8.0: Log D is 2.28 to 3.00.

The lower the Log D value is, the less is lipophilicity and the more is surface retention and mucosal effectiveness. Conversely, the higher the Log D value is, the more is lipophilicity, and the more is mucosal penetration and submucosal permeation.

Brimonidine has the following Log D values at different pH:
pH 4.0 to 6.2: Log D is -1.02 to -0.44;
pH 7.0 to 8.0: Log D is 0.55 to 0.79.

When the selective α-2 agonist is brimonidine, the moderate lipophilicity is achieved at pH of between 6.2 and 6.8. A pH of less than 6.2 is preferred to achieve greater mucosal surface retention, and a pH of greater than 6.8 is preferred to achieve greater mucosal penetration and submucosal permeation.

In one embodiment, the invention provides an aqueous composition for treating a nasal condition consisting essentially of brimonidine, wherein said brimonidine concentration is from between about 0.03% to about 0.035% weight by volume, wherein pH of said composition is between about 6.2 and about 6.8.

In another embodiment, the compositions of the invention may also include additional components, which include, but are not limited to, preservatives, delivery vehicles, tonicity adjustors, buffers, pH adjustors, antioxidants, permeation enhancers and water.

Preservatives useful in a topical composition include, but are not limited to, benzalkonium chloride, chlorobutanol, thimerosal, phenylmercuric acetate, disodium ethylenediaminetetraacetic acid ("EDTA"), phenylmercuric nitrate, or benzyl alcohol. In a preferred embodiment of the invention the preservative consists of components that have been approved for use in over-the-counter ("OTC") pharmaceutical compositions. In a more preferred embodiment the OTC suitable preservative is a mixture of disodium EDTA and benzyl alcohol. In a yet more preferred embodiment disodium EDTA is at an amount of from about 0.01% to about 0.1% w/v and benzyl alcohol is at an amount of from about 0.1% to about 1.0% w/v.

Vehicles useful in a topical composition include, but are not limited to, polyvinyl alcohol, polyvinylpyrrolidone ("povidone"), hydroxypropyl cellulose, poloxamers, carboxymethyl cellulose, hydroxyethyl cellulose and purified water or a mixture thereof It is also possible to use a physiological saline solution as a major vehicle. In a preferred embodiment of the invention the vehicle consists of components that have been approved for use in OTC pharmaceutical compositions. In a more preferred embodiment the OTC suitable vehicle is a mixture of povidone, carboxymethyl cellulose and hydroxypropyl cellulose. In a yet more preferred embodiment the carboxymethyl cellulose as a viscosity enhancer is supplemented by addition of a coprecipitate of carboxymethyl cellulose and microcrystalline cellulose; such that for a preferred embodiment the ratio of carboxymethyl cellulose to microcrystalline cellulose is from 9:91 to 13:87—such as Avicel® 591 (Avicel is a registered trademark of FMC Corporation); where other ratios may be used, including but not limited to Avicel® RTM CL-611 or Avicel® RTM RC-581. Such viscosity supplementation as occurs with coprecipitates of carboxymethyl cellulose and microcrystalline cellulose provides enhanced thixotropic properties that it is believed adds stability to preferred embodiments and helps prevent sedimentation of ingredients, particularly during prolonged storage. In another more preferred embodiment the hydroxypropyl cellulose has a viscosity of about 2920 centipoise (1% in water at 25° C.). In yet another more preferred embodiment carboxymethyl cellulose is at an amount of from about 1.0% to about 5.0% w/v, polyvinylpyrrolidone is at an amount of from about 1.0% to about 5.0% w/v and hydroxypropyl cellulose is at an amount of from about 0% to about 5% w/v.

A tonicity adjustor also can be included, if desired, in a topical composition of the invention. Such a tonicity adjustor can be, without limitation, a salt such as sodium chloride, potassium chloride, mannitol or glycerin, or another pharmaceutically or ophthalmically acceptable tonicity adjustor. In a preferred embodiment of the invention the tonicity adjustor has been approved for use in OTC pharmaceutical compositions. In a more preferred embodiment the OTC suitable tonicity adjustor is glycerin. In a yet more preferred embodiment glycerin is at an amount of from about 0.1% to about 1.0% w/v.

Various buffers and means for adjusting pH can be used to prepare topical compositions of the invention. Such buffers include, but are not limited to, acetate buffers, citrate buffers, phosphate buffers and borate buffers. It is understood that acids or bases can be used to adjust the pH of the composition as needed. In a preferred embodiment of the invention the pH adjustor has been approved for use in OTC pharmaceutical compositions. In a more preferred embodiment the OTC suitable pH adjustor is a phosphate buffer. In a yet more preferred embodiment of the invention the phosphate buffer is a mixture of sodium phosphate, dibasic and sodium phosphate, monobasic. In yet another more preferred embodiment sodium phosphate, dibasic is at an amount of from about 0.01% to about 0.1% w/v and sodium phosphate, monobasic is at an amount of from about 0.1% to about 1.0% w/v.

Topically acceptable antioxidants useful in preparing a topical composition include, yet are not limited to, sodium metabisulfite, sodium thiosulfate, acetylcysteine, butylated hydroxyanisole and butylated hydroxytoluene.

Permeation enhancers that can be used in a topical composition of the present invention include, but are not limited to, menthol and polyethylene glycol-32 ("PEG-32") or a mixture thereof. In a preferred embodiment of the invention the permeation enhancer consists of components that have been approved for use in OTC pharmaceutical compositions. In a more preferred embodiment the OTC suitable permeation enhancer is a mixture of menthol and PEG-32. In a yet more preferred embodiment PEG-32 is at an amount of from about 1.0% to about 10.0% w/v of and menthol is at an amount of from about 0.001% to about 0.1% w/v.

The compositions of the invention may be administered topically through nasal delivery or topically delivered as ophthalmic solutions into the eyes.

In one embodiment, the provided composition is an aerosolized composition. It is within a skill in the art to prepare aerosolized compositions of the present invention. The aerosolized compositions of the present invention are generally delivered via an inhaler, jet nebulizer, or ultrasonic nebulizer which is able to produce aerosol particles with size of between about 1 and 10 μm.

To make the topical compositions of the present invention, one can simply dilute, using methods known in the art, more concentrated solutions of selective α-2 agonists. The precise method of carrying out the dilutions is not critical. Any commonly used diluents, including preservatives described above in the application, suitable for topical solutions can be used.

Proper dosages of the compositions of the present invention are concentration-dependent. To determine the specific dose for a particular subject, a skilled artisan would have to take into account kinetics and absorption characteristics of the particular highly selective α-2 adrenergic receptor agonist.

The present invention is more fully demonstrated by reference to the accompanying drawings.

FIG. 1 is a graphical representation of the effects of activating α-1 adrenergic receptors. As FIG. 1 demonstrates, administering α-1 adrenergic receptor agonists leads to constriction of the proximal arteriole (on the left side) which in turn decreases the flow of blood through the capillaries and causes ischemia for the tissues downstream of arteriole.

Figure 2:
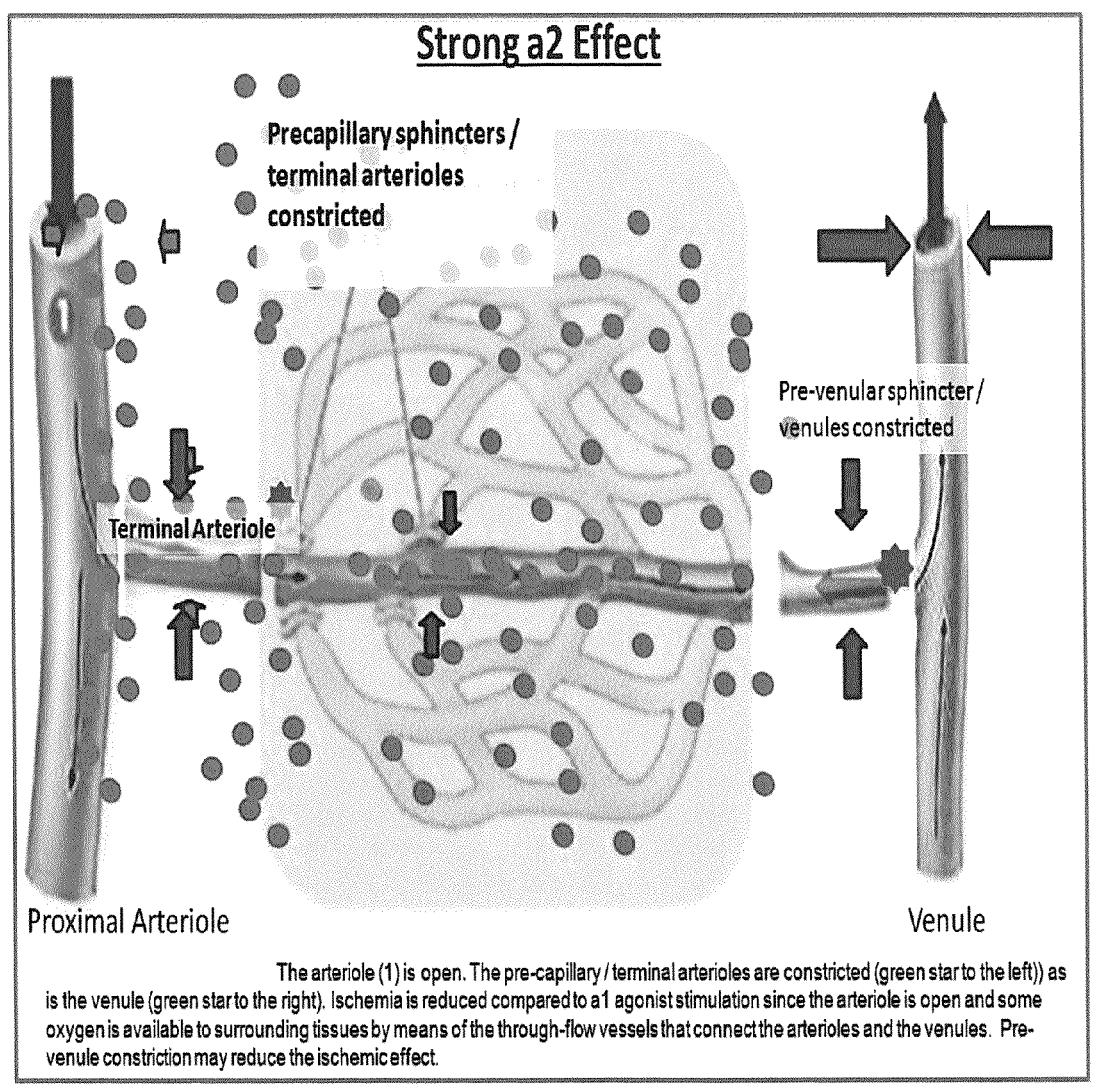
FIG. 2 is a graphical representation of the effects of preferentially activating α-2 adrenergic receptors.

FIG. 2 is a graphical representation of the effects of preferentially activating α-2 adrenergic receptors. As FIG. 2 demonstrates, administering α-2 adrenergic receptor agonists leads to constriction of the pre-capillary/terminal arteriole (on the left side) and constriction of the venule (on the right side). Ischemia is decreased, as compared to stimulating α-1 adrenergic receptors because the arteriole is open and some oxygen is available to surrounding tissues by means of the through-flow vessels that connect the arterioles and the venules. Pre-venule constriction may reduce the ischemic effect and reduce vasodilation that may contribute to nasal congestion.

The following representative embodiments are provided solely for illustrative purposes and are not meant to limit the invention in any way. Additionally, the following representative embodiments each comprise brimonidine and a group of excipients that have been used in OTC pharmaceuticals.

Representative Embodiments

In a more preferred embodiment the composition comprises:
  0.035% w/v brimonidine;
  3.0% w/v Avicel® 591;
  3.0% w/v polyvinylpyrrolidone;
  5.0% w/v polyethylene glycol-32;
  0.0975% w/v sodium phosphate, dibasic;
  0.5525% w/v sodium phosphate, monobasic;
  0.03% w/v disodium EDTA;
  0.25% w/v benzyl alcohol;
  0.5% w/v glycerin;
  0.00375% w/v menthol; and
  0.0% w/v hydroxypropyl cellulose.

In another more preferred embodiment the composition comprises:
  0.035% w/v brimonidine;
  3.0% w/v Avicel® 591;
  3.0% w/v polyvinylpyrrolidone;
  5.0% w/v polyethylene glycol-32;
  0.0975% w/v sodium phosphate, dibasic;
  0.5525% w/v sodium phosphate, monobasic;
  0.03% w/v disodium EDTA;
  0.25% w/v benzyl alcohol;
  0.5% w/v glycerin;
  0.00375% w/v menthol; and
  1.0% w/v hydroxypropyl cellulose.

In another more preferred embodiment the composition comprises:
  0.035% w/v brimonidine;
  3.0% w/v Avicel® 591;
  3.0% w/v polyvinylpyrrolidone;
  5.0% w/v polyethylene glycol-32;
  0.0975% w/v sodium phosphate, dibasic;
  0.5525% w/v sodium phosphate, monobasic;
  0.03% w/v disodium EDTA;
  0.25% w/v benzyl alcohol;
  0.5% w/v glycerin;
  0.00375% w/v menthol; and
  2.0% w/v hydroxypropyl cellulose.

In a more preferred embodiment the composition comprises:
  0.035% w/v brimonidine;
  3.0% w/v Avicel® 591;
  3.0% w/v polyvinylpyrrolidone;
  5.0% w/v polyethylene glycol-32;
  0.0975% w/v sodium phosphate, dibasic;
  0.5525% w/v sodium phosphate, monobasic;
  0.03% w/v disodium EDTA;
  0.25% w/v benzyl alcohol;
  0.5% w/v glycerin;
  0.015% w/v menthol; and
  2.0% w/v hydroxypropyl cellulose.

Method of Preparation

Preferred compositions of the present invention were prepared by first dissolving brimonidine, PEG-32, disodium EDTA, and sodium phosphate, monobasic in water. Next, polyvinylpyrrolidone was mixed into the composition until dissolved. Benzyl alcohol and glycerin were mixed into the composition prior to the completion of the dissolution of polyvinylpyrrolidone. Next, Avicel 591® was mixed in as a thickening agent along with water until the composition was about 80% of final volume. Upon completion of the dissolution of Avicel® 591, Menthol was mixed into the composition. Next, hydroxypropyl cellulose was added into the composition and left to mix for at least one hour. Finally, water was added to the final volume and pH was adjusted to 5.5.

It is clear to an expert in the art that certain substituions to the above formulations are consistent with its effectiveness, such as replacing hydroxylpropyl cellulose with other viscosity enhancers, particularly other cellulose derivates such as hydroxylpropyl, ethyl, or methyl cellulose; use of PEG of other molecular weights, including but not limited to low molecular weight PEG 400 which may offer greater penetration of tenacious mucosal secretions more common to certain types of nasal congestion.

What is claimed is:

1. A composition comprising:
brimonidine, or a pharmaceutically acceptable salt thereof;
a preservative consisting of a mixture of disodium ethylenediaminetetraacetic acid at an amount of from about 0.01% to about 0.1% w/v and benzyl alcohol at an amount of from about 0.1% to about 1.0% w/v;
a vehicle consisting of a mixture of a coprecipitate containing carboxymethyl cellulose and microcrystalline cellulose at an amount of from about 1.0% to about 5.0% w/v, wherein the ratio of carboxymethyl cellulose to microcrystalline cellulose is from about 9:91 to about 13:87, polyvinylpyrrolidone at an amount of from about 1.0% to about 5.0% w/v and hydroxypropyl cellulose at an amount of from about 0% to about 5% w/v;
a tonicity adjustor consisting of glycerin at an amount of from about 0.1% to about 1.0% w/v;
a pH adjustor consisting of a mixture of sodium phosphate, dibasic at an amount of from about 0.01% to about 0.1% w/v and sodium phosphate, monobasic at an amount of from about 0.1% to about 1.0% w/v; and
a permeation enhancer consisting of a mixture of a polyethylene glycol at an amount of from about 1.0% to about 10.0% w/v and menthol at an amount of from about 0.001% to about 0.1% w/v;
wherein the brimonidine is at an amount of from about 0.03% to about 0.035% w/v, wherein pH of the composition is between about 5.0 and about 8.0, and wherein w/v denotes weight by volume.

2. A method of treating a nasal condition in a subject in need thereof comprising administering to the subject a pharmaceutically effective amount of the composition of claim 1.

3. The composition of claim 1 wherein:
the brimonidine is at an amount of about 0.035% w/v;
the coprecipitate is Avicel 591® at an amount of about 3.0% w/v;
the polyvinylpyrrolidone is at an amount of about 3.0% w/v;
the polyethylene glycol is polyethylene glycol-32 at an amount of about 5.0% w/v;
the sodium phosphate, dibasic is at an amount of about 0.0975% w/v;
the sodium phosphate, monobasic is at an amount of about 0.5525% w/v;
the disodium ethylenediaminetetraacetic acid is at an amount of about 0.03% w/v;
the benzyl alcohol is at an amount of about 0.25% w/v;
the glycerin is at an amount of about 0.5% w/v;
the menthol is at an amount of about 0.00375% w/v;
the hydroxypropyl cellulose is at an amount of about 0.0% w/v.

4. The composition of claim 1 wherein:
the brimonidine is at an amount of about 0.035% w/v;
the coprecipitate is Avicel 591® at an amount of about 3.0% w/v;
the polyvinylpyrrolidone is at an amount of about 3.0% w/v;
the polyethylene glycol is polyethylene glycol-32 at an amount of about 5.0% w/v;
the sodium phosphate, dibasic is at an amount of about 0.0975% w/v;
the sodium phosphate, monobasic is at an amount of about 0.5525% w/v;
the disodium ethylenediaminetetraacetic acid is at an amount of about 0.03% w/v;
the benzyl alcohol is at an amount of about 0.25% w/v;
the glycerin is at an amount of about 0.5% w/v;
the menthol is at an amount of about 0.00375% w/v;
the hydroxypropyl cellulose is at an amount of about 1.0% w/v.

5. The composition of claim 1 wherein:
the brimonidine is at an amount of about 0.035% w/v;
the coprecipitate is Avicel 591® at an amount of about 3.0% w/v;
the polyvinylpyrrolidone is at an amount of about 3.0% w/v;
the polyethylene glycol is polyethylene glycol-32 at an amount of about 5.0% w/v;
the sodium phosphate, dibasic is at an amount of about 0.0975% w/v;
the sodium phosphate, monobasic is at an amount of about 0.5525% w/v;
the disodium ethylenediaminetetraacetic acid is at an amount of about 0.03% w/v;
the benzyl alcohol is at an amount of about 0.25% w/v;
the glycerin is at an amount of about 0.5% w/v;
the menthol is at an amount of about 0.015% w/v;
the hydroxypropyl cellulose is at an amount of about 2.0% w/v.

6. A composition comprising:
brimonidine or a pharmaceutically acceptable salt thereof at an amount of about 0.035% w/v;
Avicel 591® at an amount of about 3.0% w/v;
polyvinylpyrrolidone at an amount of about 3.0% w/v;
polyethylene glycol-32 at an amount of about 5.0% w/v;
sodium phosphate, dibasic at an amount of about 0.0975% w/v;
sodium phosphate, monobasic at an amount of about 0.5525% w/v;
disodium EDTA at an amount of about 0.03% w/v;
benzyl alcohol at an amount of about 0.25% w/v;
glycerin at an amount of about 0.5% w/v;
menthol at an amount of about 0.00375% w/v; and
hydroxypropyl cellulose at an amount of about 2.0% w/v, wherein w/v denotes weight by volume.

7. A method of treating a nasal condition in a subject in need thereof comprising administering to said subject a pharmaceutically effective amount of the composition of claim 6.

8. The method of claim 7 wherein the nasal condition is selected from the group consisting of insufficient nares patency for peak athletic performance, rhinitis medicamentosa secondary to oxymetazoline nasal spray, allergic rhinitis, vasomotor rhinitis, sleep apnea, nasal secretion induced gastroesophogeal reflux, sleep apnea due to obstructed or partially obstructed turbinates, and treatment of partial or complete nasal obstruction due to nasal polyps or a combination thereof.

* * * * *